(12) United States Patent
Jamali

(10) Patent No.: US 8,998,918 B2
(45) Date of Patent: Apr. 7, 2015

(54) DEVICE AND METHOD FOR ALLOGRAFT AND TISSUE ENGINEERED OSTEOCHONDRAL GRAFT SURFACE MATCHING, PREPARATION, AND IMPLANTATION

(76) Inventor: Amir Jamali, Sacramento, CA (US)

( * ) Notice: Subject to any disclaimer, the term of this patent is extended or adjusted under 35 U.S.C. 154(b) by 454 days.

(21) Appl. No.: 12/370,465

(22) Filed: Feb. 12, 2009

(65) Prior Publication Data
US 2009/0209962 A1 Aug. 20, 2009

Related U.S. Application Data

(60) Provisional application No. 61/028,153, filed on Feb. 12, 2008.

(51) Int. Cl.
*A61B 17/58* (2006.01)
*A61B 17/60* (2006.01)
*A61F 2/00* (2006.01)
*A61B 17/16* (2006.01)
*A61F 2/28* (2006.01)
*A61F 2/30* (2006.01)
*A61F 2/46* (2006.01)

(52) U.S. Cl.
CPC .............. *A61B 17/1635* (2013.01); *A61F 2/28* (2013.01); *A61F 2/30756* (2013.01); *A61F 2/4644* (2013.01); *A61B 17/1637* (2013.01); *A61B 17/1675* (2013.01); *A61B 17/1684* (2013.01); *A61F 2/30942* (2013.01); *A61F 2002/30224* (2013.01); *A61F 2002/30764* (2013.01); *A61F 2230/0069* (2013.01)

(58) Field of Classification Search
USPC ..................... 606/80, 81, 96–98, 88
See application file for complete search history.

(56) References Cited

U.S. PATENT DOCUMENTS

| | | | |
|---|---|---|---|
| 3,686,922 A | 8/1972 | Bley | |
| 3,741,706 A | 6/1973 | Conley | |
| 4,904,265 A | 2/1990 | MacCollum | |
| 5,176,711 A | 1/1993 | Grimes | |
| 5,312,411 A * | 5/1994 | Steele et al. | 606/88 |
| 5,320,626 A | 6/1994 | Schmieding | |
| 5,329,846 A | 7/1994 | Bonutti | |
| 5,423,823 A | 6/1995 | Schmieding | |
| 5,713,374 A | 2/1998 | Pachence | |
| 5,782,835 A | 7/1998 | Hart | |
| 5,824,078 A | 10/1998 | Nelson | |
| 5,919,196 A | 7/1999 | Bobic et al. | |
| 6,156,069 A | 12/2000 | Amstutz | |
| 6,358,253 B1 | 3/2002 | Torrie | |
| 6,458,161 B1 | 10/2002 | Gibbs | |
| 6,488,033 B1 | 12/2002 | Cerundolo | |
| 6,591,581 B2 | 7/2003 | Schmieding | |
| 6,595,999 B2 | 7/2003 | Marchione | |

(Continued)

OTHER PUBLICATIONS

Bugbee, W., "Fresh Osteochondral Allografts." Semin Arthroplasty 11.4 (2000): 1-7.

(Continued)

*Primary Examiner* — David Bates
*Assistant Examiner* — Samuel Hanna
(74) *Attorney, Agent, or Firm* — Craig M. Stainbrook; Stainbrook & Stainbrook, LLP

(57) ABSTRACT

A device and technique for the preparation and implantation of osteochondral allografts for resurfacing of a human joint. The grafts are prepared to a uniform shell thickness using the described invention.

7 Claims, 16 Drawing Sheets

(56) References Cited

U.S. PATENT DOCUMENTS

| | | | |
|---|---|---|---|
| 7,160,305 B2 | 1/2007 | Schmieding | |
| 7,241,315 B2 | 7/2007 | Evans | |
| 7,264,634 B2 | 9/2007 | Schmieding | |
| 2002/0082704 A1* | 6/2002 | Cerundolo | 623/20.35 |
| 2003/0130741 A1 | 7/2003 | McMinn | |
| 2003/0163137 A1* | 8/2003 | Smucker et al. | 606/87 |
| 2003/0187514 A1 | 10/2003 | McMinn | |
| 2004/0148030 A1* | 7/2004 | Ek | 623/20.14 |
| 2006/0178748 A1* | 8/2006 | Dinger et al. | 623/18.11 |
| 2007/0135918 A1 | 6/2007 | Malinin | |
| 2007/0162038 A1 | 7/2007 | Tuke | |
| 2008/0255623 A1* | 10/2008 | Steiner et al. | 606/86 R |

OTHER PUBLICATIONS

Bugbee, W.D. and Convery, F.R. "Osteochondral Allograft Transplantation." ClinSports Med 18.1 (1999): 67-75.

Bugbee, W.D., et al. "Fresh Osteochondral Allografting of the Patellofemoral Joint." Proceedings of the 69th Annual Meeting of the American Academy of Arthopaedic Surgeons. San Francisco, CA, 2001.

Emmerson, B.C., et al. "Fresh Ostechondral allografting in the Treatment of Osteochondritis Dissecans of the Femoral Condyle." American Journal of Sports Medicine 35.6 (2007): 907-14.

Jamali, A.A. et al. "Fresh Osteochondral Allografts: Results in the Patellofemoral Joint." Clin Orthop Relat Res. 437 (2005): 176-85.

Jamali, A.A.; Hatcher, S.L.; and You, Z. "Donor Cell Survival in a Fresh Osteochondral Allograft at Twenty-Nine Years. A Case Report." J Bone Joint Surg Am 39.1 (2007): 166-9.

Meyers, M.H. "Resurfacing of the Femoral Head with Fresh Osteochondral Allografts. Long Term Results." Clin Ortop. 197 (1985): 111-4.

Allograft OATS surgical technique. Arthrex.

McMinn, D. "Smith & Nephew Birmingham Hip Resurfacing Surgical Technique"; Booklet dated Apr. 2006, Smith & Nephew, Memphis, TN, USA, 36 pgs.

* cited by examiner

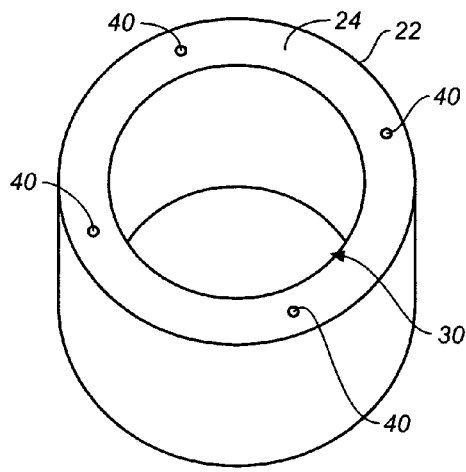
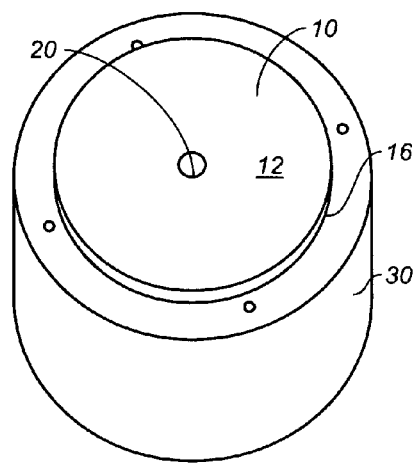
FIG. 2A  FIG. 2B
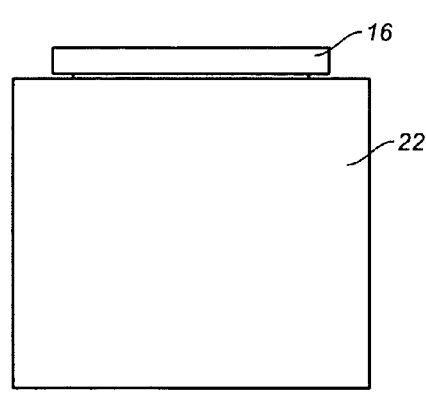
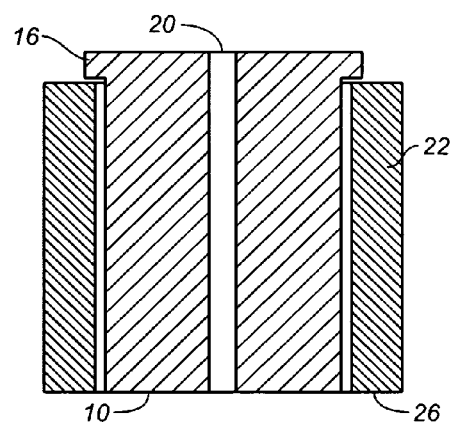
FIG. 2C  FIG. 2D

DEVICE AND METHOD FOR ALLOGRAFT AND TISSUE ENGINEERED OSTEOCHONDRAL GRAFT SURFACE MATCHING, PREPARATION, AND IMPLANTATION

CROSS REFERENCES TO RELATED APPLICATIONS

The present application claims the benefit of the filing date of U.S. Provisional Patent Application Ser. No. 61/028,153, filed Feb. 12, 2008.

SEQUENCE LISTING

Not applicable.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION

1. Field of the Invention

The present invention relates generally to methods and apparatus for orthopedic joint repair and reconstruction, and more particularly to a novel set of surgical instruments and a method of using the same for the preparation and implantation of osteochondral allografts for resurfacing of the hip joint, knee joint, and shoulder joint. The grafts are prepared to a uniform shape and peripheral topography to the topography of the recipient site.

2. Discussion of Related Art Including Information Disclosed Under 37 CFR §§1.97, 1.98

Reconstruction of joints remains an ongoing area of investigation. Since the work of Erich Lexer in the early part of the twentieth century, entire joints have been transplanted into human patients. These large grafts termed "allografts" were associated with high failure rates and cartilage degeneration. Additionally, the transplant recipient was required to immobilize the joint and to avoid bearing weight on the transplant for long periods of time.

In the early 1970's, the concept of shell allografts consisting of fresh bone and cartilage was introduced. With these grafts, only a thin shell of bone was transplanted. The thin bone shell essentially functioned as a carrying vehicle for the fresh articular cartilage that would remain populated with cells from the donor. Once the bone of the host healed to the graft bone, the articular cartilage would continue to receive nutrition from the synovial fluid in the joint. The bone, due to its small volume, generated a minimal immune response. Using this technique, large areas of articular cartilage could be repaired with normal cartilage with no need for systemic immunosuppressive medications. The success of this surgical procedure is well documented and is based on both clinical improvements as well as documented long-term donor cell viability (nearly 30 years after the transplantation).

Tissue engineering can be defined as a multidisciplinary field applying the principles of engineering and biological sciences with the goal of regeneration and/or restoration of tissues and organs. Up to the present time the major areas of clinical application of tissue engineering in orthopaedic surgery have been in autologous chondrocyte implantation, in which cells from a donor cartilage are pre-harvested, cultured, and then injected into the recipient under a periosteal or synthetic patch with the aim of forming mature hyaline-like cartilage. The principal efforts in this field are now being directed at manufacturing complete tissues that include both cartilaginous and osseous components of the joint surface in order to optimize healing of the artificial tissue to the recipient bone. However, to date no osteochondral tissue engineered constructs for cartilage repair have been widely used in humans. Were such an implant to be developed, a method will be required to prepare the recipient site precisely based on its surface characteristics so as to accommodate the implant with a flush joint surface.

In the area of osteochondral allograft instrumentation, the emphasis has been on cylindrical instrumentation to prepare cores that can be trimmed and transplanted into cylindrically prepared recipient sites in the complementary portion of the joint. In U.S. Pat. No. 6,488,033, to Cerundolo, there is described a method of obtaining and placing an osteochondral allograft in substantially the same orientation as the damaged segment of the bone which is initially removed from the patient. With this technique, the surface of the transplanted plug is matched to the contour of the excised osteochondral tissue. However, the placement of the guides is essentially dependent on free hand techniques and the guides do not provide a precise match with the complex contours of the cartilaginous surface.

U.S. Pat. No. 6,591,581, to Schmieding, teaches a method and instrumentation for the preparation, distribution, and insertion of round, size specific osteochondral allografts. The distribution network for fresh osteochondral allograft cores is laid out, along with some details for instrumentation in preparing such osteochondral plugs and recipient sites. This instrumentation is analogous to that discussed in U.S. Pat. No. 5,919,196, to Bobic et al, for autologous osteochondral transfer, otherwise known as mosaicplasty. However, no insights are offered by these publications into meeting the challenges of preparing a perfect surface match for these large osteochondral cylindrical grafts.

BRIEF SUMMARY OF THE INVENTION

The present invention relates to a specialized device for the preparation of large cylindrical grafts up to 40 mm in diameter with precise surface matching of the donor and recipient. The perfect matching is due to the inventive instrumentation, which may be manufactured with matched pairs of inner and outer guides with a large number of surface contours that can be sequentially trailed on the surface to be grafted. Once a good match is obtained on the recipient cartilage surface, the same guides can be placed on the graft to find a perfect surface contour match, and this match may or may not be from the same location and orientation as the recipient site. With this technology, the precision of the surgical procedure for fresh osteochondral allografting can be improved, and the preparation of tissue engineered osteochondral constructs will be simplified when they become available.

Osteochondral allografts have a long history of clinical success in the treatment of articular cartilage defects. One of the most commonly used techniques for osteochondral allografting has been the use of press-fit allograft cores placed into a recipient defect. Surface matching of these cores to provide a smooth transition from graft to native cartilage has been a technical challenge. The present invention is aimed at addressing this issue by preparing precontoured guides using manual technology, such as molds, or using computer technology, such as rapid prototyping, in such a way that the articular surface of the guides precisely matches the articular surface of both the allograft and the recipient bone. Once each of the guides are placed on the articular surface of either the donor or the recipient cartilage, guidepins can be used to secure the guides in such a way that the allograft core obtained and implanted leads to a precise surface match between the donor and recipient cartilage. This technology can be employed in transplant procedures for a variety of large joints including but not limited to the knee, shoulder, hip, and ankle joints.

Other novel features characteristic of the invention, together with further objects and advantages thereof, will be better understood from the following description considered in connection with the accompanying drawings, in which preferred embodiments of the invention are illustrated by way of example. It is to be expressly understood, however, that the drawings are for illustration and description only and are not intended as a definition of the limits of the invention. The various features of novelty that characterize the invention are pointed out with particularity in the claims annexed to and forming part of this disclosure. The invention does not reside in any one of these features taken alone, but rather in the particular combination of all of its structures for the functions specified.

There has thus been broadly outlined the more important features of the invention in order that the detailed description thereof that follows may be better understood, and in order that the present contribution to the art may be better appreciated. There are, of course, additional features of the invention that will be described hereinafter and which will form additional subject matter of the claims appended hereto. Those skilled in the art will appreciate that the conception upon which this disclosure is based readily may be utilized as a basis for the designing of other structures, methods and systems for carrying out the several purposes of the present invention. It is important, therefore, that the claims be regarded as including such equivalent constructions insofar as they do not depart from the spirit and scope of the present invention.

BRIEF DESCRIPTION OF THE SEVERAL VIEWS OF THE DRAWINGS

The detailed description that follows makes reference to the annexed drawings wherein:

FIG. 2A is an upper perspective view of the non-contoured outer guide;

FIG. 2B is an upper perspective view showing the non-contoured inner guide inserted into the non-contoured outer guide;

FIG. 2C is a side view in elevation thereof;

FIG. 2D is a cross-section side view in elevation thereof;

FIG. 6A is a perspective views showing the recipient site reamer disposed in alignment with a reaming site immediately above a femur, while

FIG. 8A is a cross-sectional schematic view of a coring reamer, while

FIG. 9A is a perspective view showing the outer contoured guide assembled with guidewires and with a coring reamer inserted therethrough, while

FIG. 10A is an upper perspective view showing the allograft femoral trochlea, while

FIG. 11A is a perspective view generally taken from the side showing the recipient femoral trochlea, while

FIG. 14A is a perspective view schematically showing the human knee, while

DETAILED DESCRIPTION OF THE INVENTION

Figure 1A:
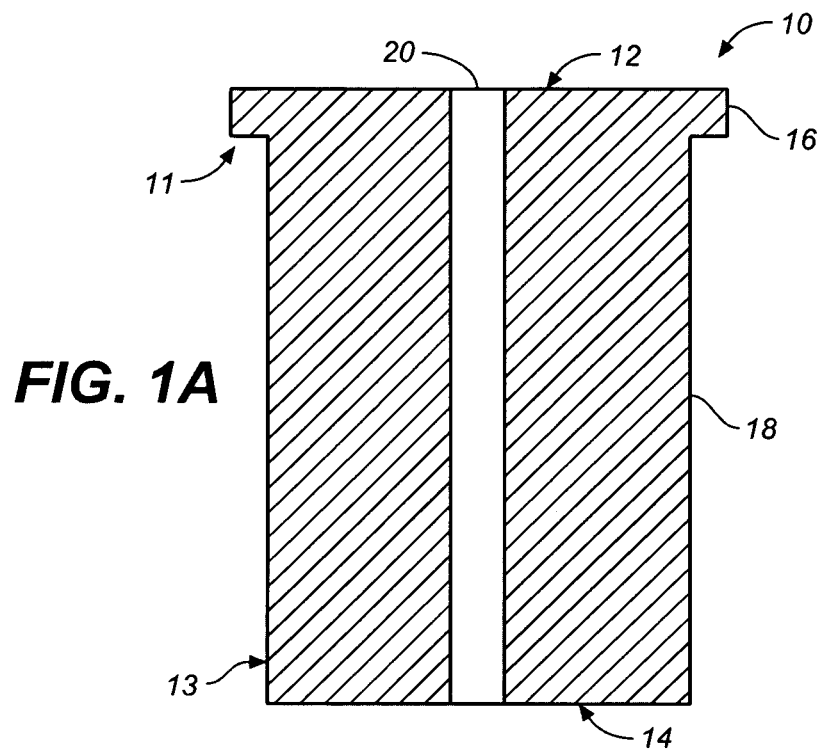
FIGS. 1A and 1B are, respectively, a cross-sectional side view in elevation and an upper perspective view of the non-contoured inner guide employed in the inventive method and apparatus.
Figure 1B:
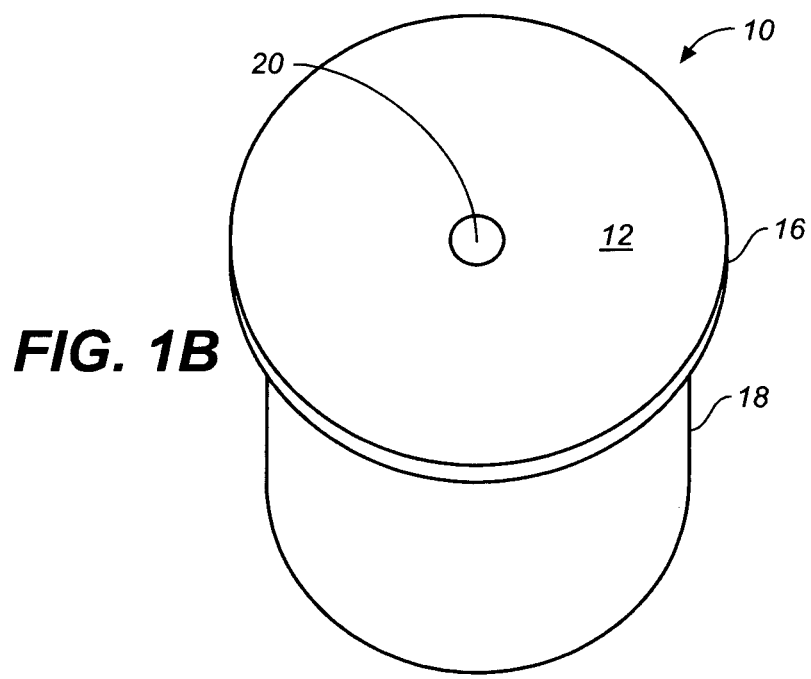

FIGS. 1A through 2D are a schematic cross-sectional and schematic perspective representation, respectively, of a non-contoured inner guide 10 and non-contoured outer guide 22. The non-contoured inner guide consists of a superior end 11 having a generally planar superior surface 12 and an inferior end 13 having a generally planar inferior surface 14, the superior surface having a circumferential expansion (rim) 16 that allows seating onto the outer guide superior edge 24. The body 18 of the non-contoured guide is cylindrical. The inner guide also contains an axially disposed central aperture 20, or through hole, that extends from the superior surface to the inferior surface and will accommodate a stabilizing guidepin of variable diameter.

The non-contoured outer guide 22 (as shown in FIGS. 2A through 2D) is a tubular or cylindrical sleeve having a flat superior end 24 and a flat inferior end 26 and an inner aperture 30. The diameter of the inner aperture is only slightly larger than the outer diameter of the matching non-contoured inner guide 10, perhaps between 0.1 and 1.0 mm, for tight tolerances. The height of the outer guide is identical to the height of the body portion 18 inferior to the rim 16 of the matching inner guide. The outer guide also contains between two and six spaced apart peripheral, circumferentially disposed and axially oriented through holes or apertures 40 (four shown in FIG. 2A) to accommodate small guidewires for stabilizing the outer guide to bone as needed for recipient site preparation and donor allograft core harvesting and to identify and fix the geometric center of both the donor osteochondral allograft core and the recipient site. The diameter of these apertures is between 0.8 and 3 mm.

In FIGS. 2B and 2C, the non-contoured inner and outer guides are combined simply by inserting the body portion of the non-contoured inner guide into the central aperture of the outer guide. FIG. 2D, is a schematic cross-sectional side view in elevation of this combination. When so inserted, the rim of the inner guide seats onto the upper or superior end of the outer guide and brings the planar inferior surface of the inner guide into co-planar relationship with the flat inferior end of the outer guide.

The non-contoured inner and outer guides can be refashioned and prepared in such a way that they exactly match a variety of contours of the articular geometry of a specified joint. In this way they can be placed so that a guidepin placed through the aperture 20 in the inner guide is oriented precisely to allow harvest of an allograft with identical surface geometry and peripheral contour as the surface geometry and peripheral contour in the recipient joint.

Figure 3A:
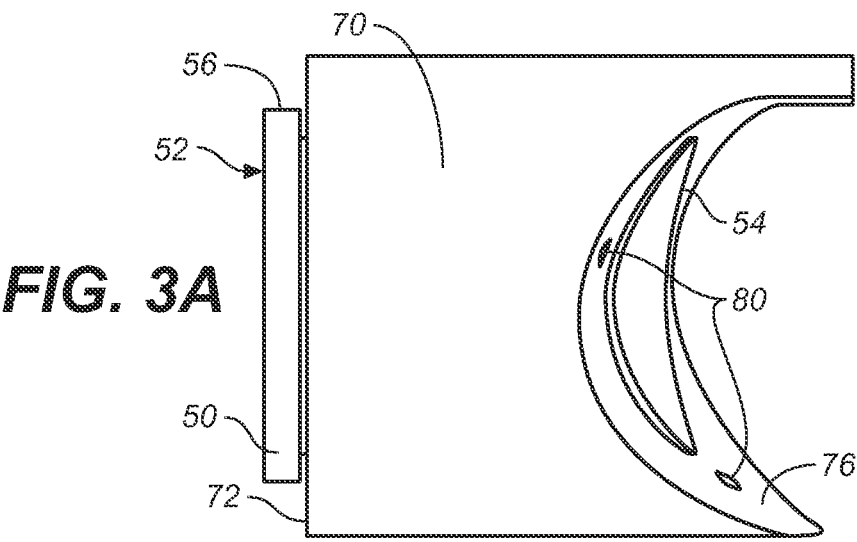
FIG. 3A is a perspective view, generally taken from a side elevation, showing an inner contoured guide combined with an outer contoured guide.
Figure 3B:
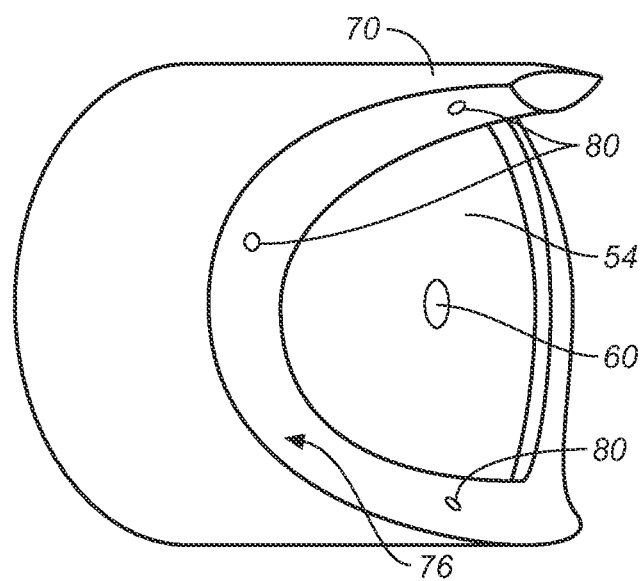
FIG. 3B is a perspective view, generally taken from the contoured end, thereof.

FIG. 3A is a lateral perspective view of a contoured inner guide 50 and a contoured outer guide 70 specific to a femoral trochlea of a human knee. The contoured inner guide 50 includes a substantially cylindrical body, a substantially planar superior surface 52, a contoured inferior end 54, an expanded circumferential rim 54 encircling the body 56 proximate the superior surface, and a central aperture 60 or through hole running axially the entire length or height of the contoured inner guide.

The contoured outer guide 70 includes a substantially planar upper rim or end 72 onto which the expanded circumferential rim 56 of the contoured inner guide is seated when it is inserted into the central aperture 74 (see esp. FIG. 7B) of the contoured outer guide. The contoured outer guide further includes a contoured inferior end 76 having a plurality of spaced apart peripheral, circumferentially oriented apertures 80 for the placement of stabilizing guidewires.

Figure 4A:
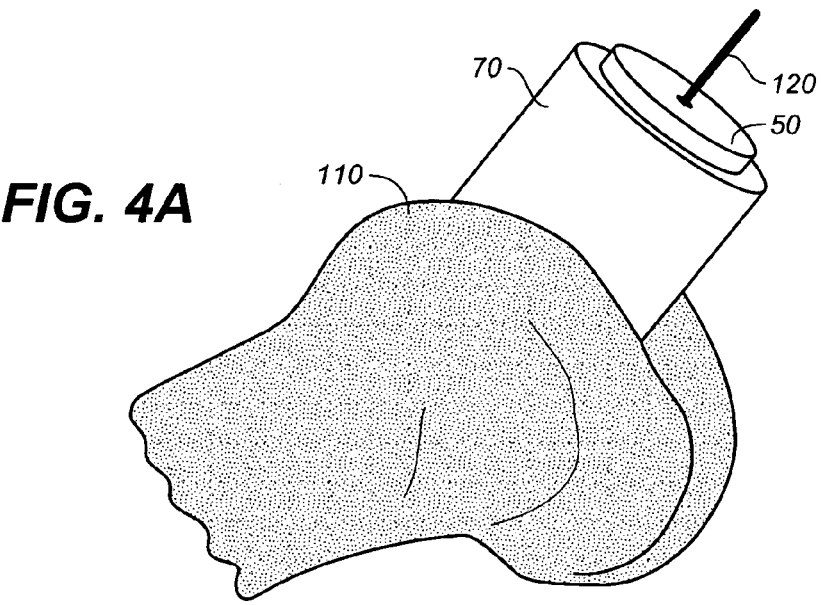
FIGS. 4A and 4B are each perspective views showing placement of the contoured guides on the femoral trochlea using a guidepin.
Figure 4B:
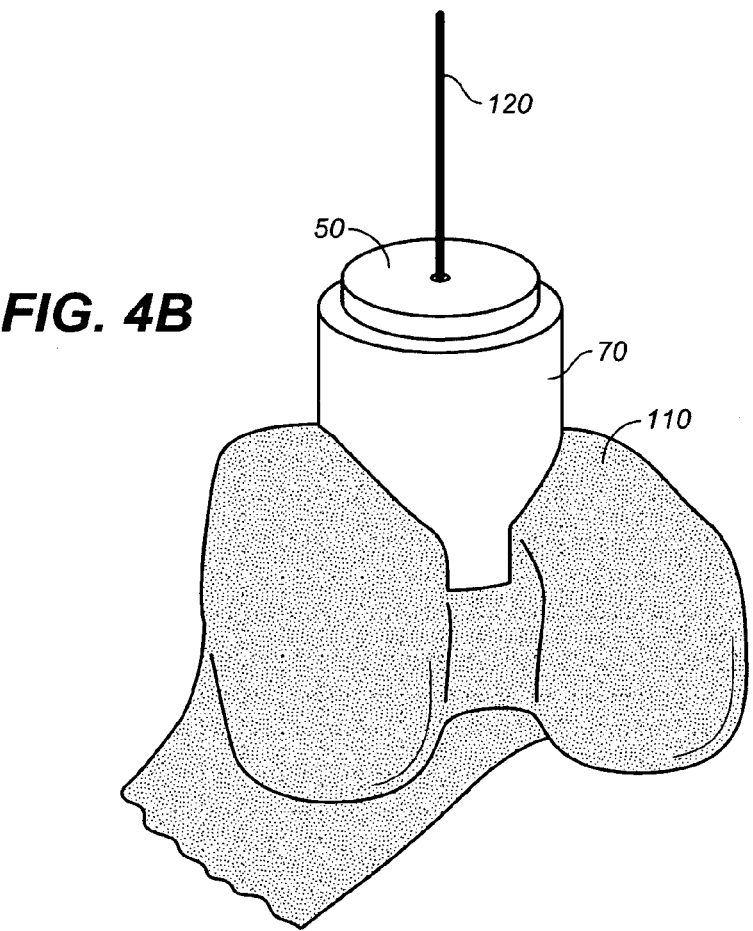

In FIGS. 4A and 4B, the combined inner contoured guide 50 and outer contoured guide 70 are placed on the exactly matched surface of the femoral trochlea 110 of the recipient in such a way that there is circumferential contact with the articular cartilage of the recipient area by both guides. Once this has been performed, a central guidepin 120 is passed through the central aperture of the contoured inner guide 50, stabilizing both guides in place. Next, the contoured inner and outer guides are removed, leaving the central guidepin in place.

Figure 5A:
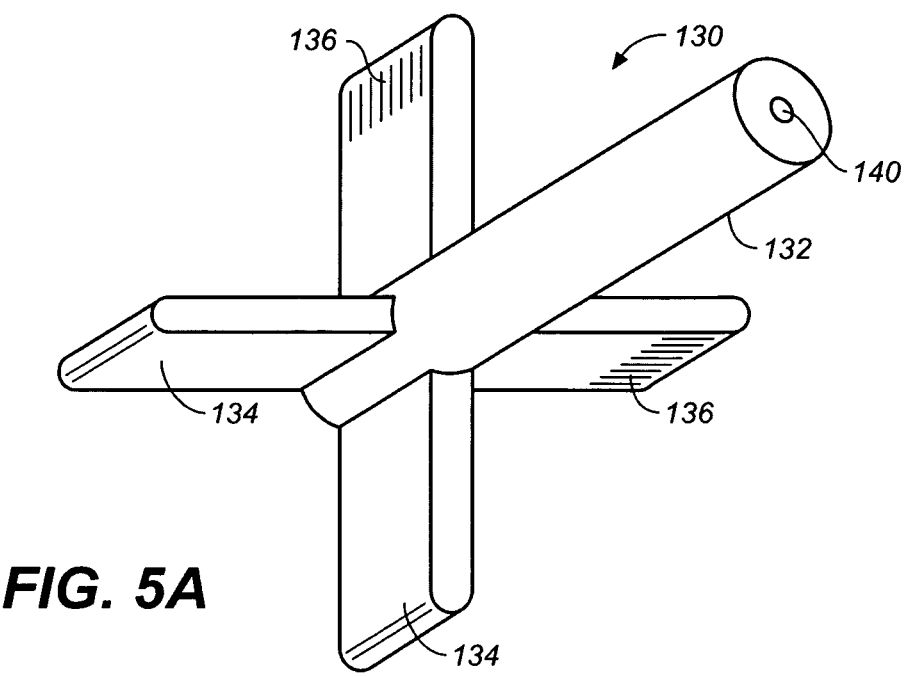
FIGS. 5A and 5B are first and second end perspective views of a reamer employed in prepared the recipient site.
Figure 5B:
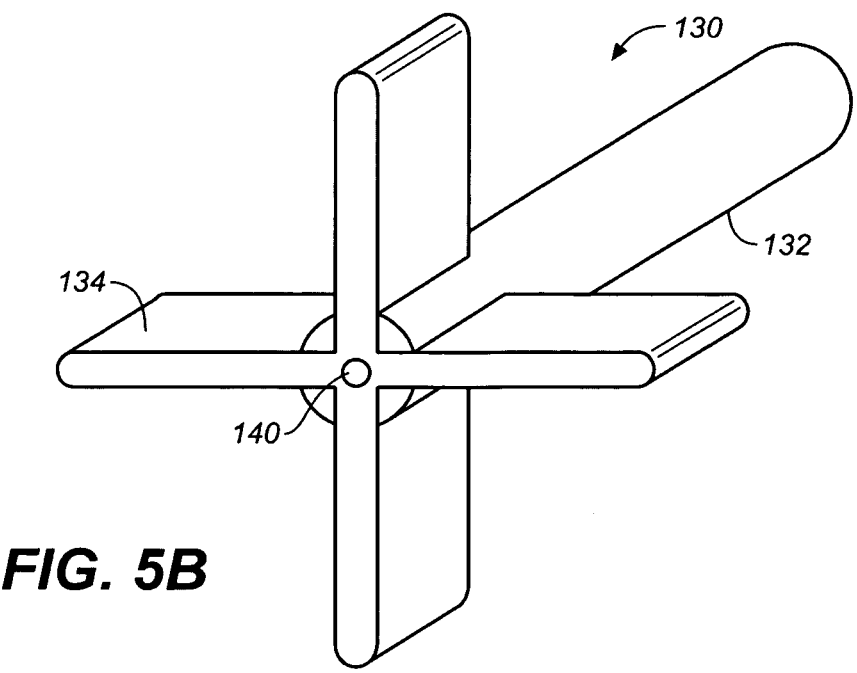

In FIGS. 5A and 5B, there is shown a recipient site reamer 130, which is an instrument with elongate tubular body 132 operatively attached to a rotating power source (not shown) at its superior aspect. At its inferior aspect the reamer consists of between three and eight sharp radially disposed blades 134 (four shown in FIGS. 5A and 5B). The reamer also has an axially disposed central aperture or through hole 140 of between 0.8 and 3.0 mm which can accommodate the guidepin 120 shown in FIG. 4, and it is disposed over the guidepin to index and orient the reamer for precise drilling. Depth markers 136 are inscribed or otherwise placed on each of the blades of the recipient site reamer to give the surgeon an estimate of the depth of preparation of the recipient site.

The contoured outer guide 70 includes a substantially planar upper rim or end 72 onto which the expanded circumferential rim 56 of the contoured inner guide is seated when it is inserted into the central aperture 74 (see esp. FIG. 3A-) of the contoured outer guide. The contoured outer guide further includes a contoured inferior end 76 having a plurality of spaced apart peripheral, circumferentially oriented apertures 80 for the placement of stabilizing guidewires.

Figure 7A:
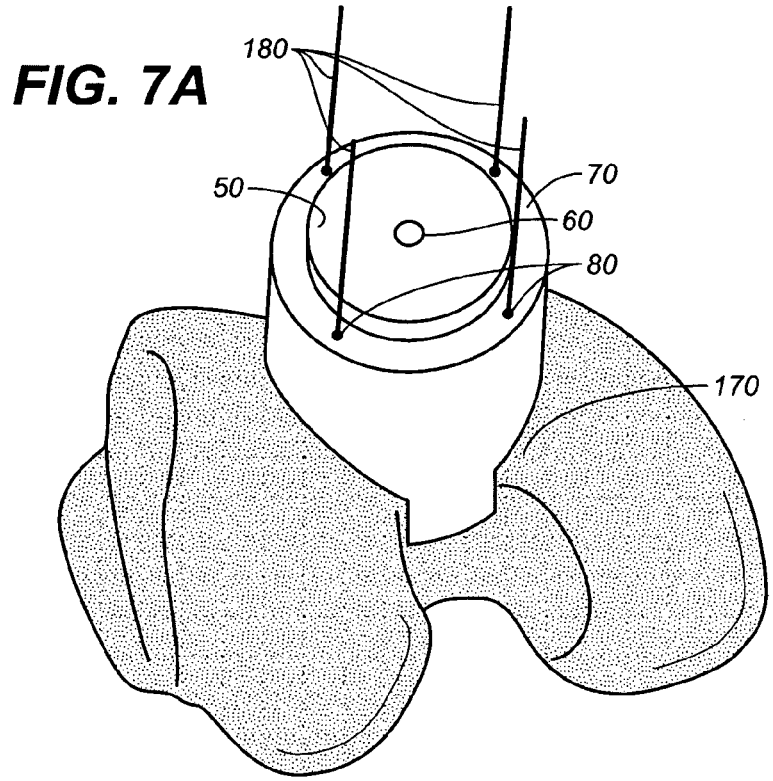
FIGS. 7A and 7B are perspective views showing an allograft femur with inner and outer guides in place and held in place with guidewires.
Figure 7B:
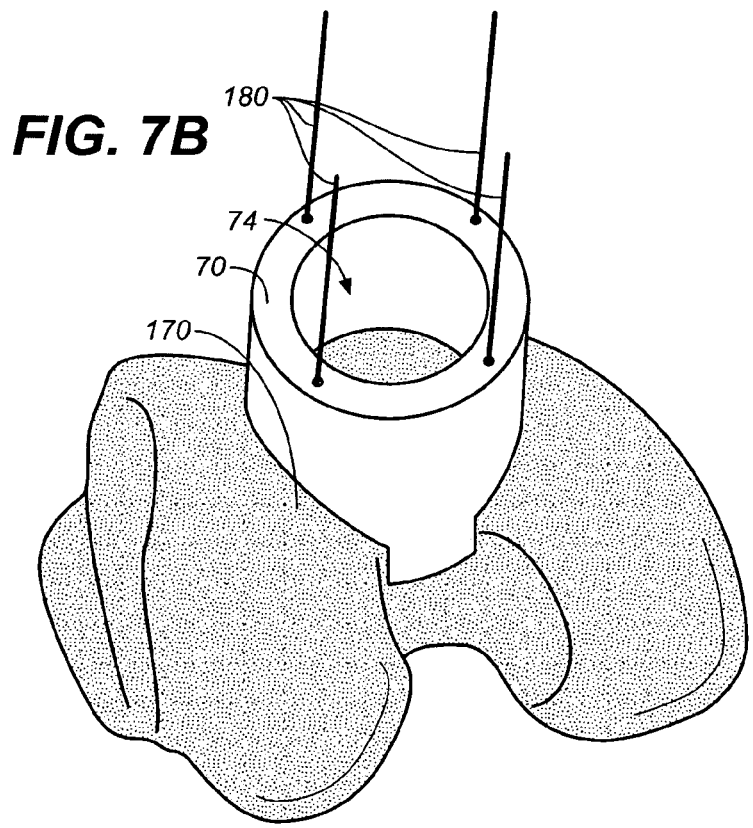

FIG. 7A is a perspective view of a donor femoral allograft trochlea 170 with the inner contoured guide 50 and the outer contoured guide 70 placed on the surface such that full contact is achieved on both guides. Next, the apertures of the outer guide 80 are used to fix the outer guide to the allograft using small guidewires 180. Subsequently, the inner guide is removed as shown in FIG. 7B.

Figure 8A:
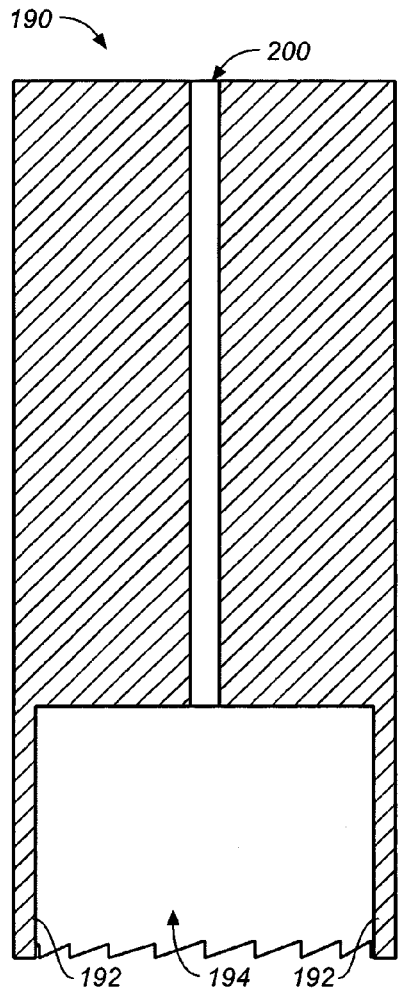

FIG. 8A is a schematic cross-sectional side view in elevation of a cylindrical coring reamer 190 used for preparing a perfectly cylindrical allograft core. The inner diameter of the reamer is between 0.1 and 1.5 mm larger than the outer diameter of the recipient site reamer (or the radius of the reamer as measured from the center of the central aperture 140 to the outer edge or tip of any of the radially disposed blades) as shown in FIG. 5. This facilitates a press-fit fixation of the allograft. The coring reamer is essentially a tubular hole-saw with a plurality of cutting teeth 192 at its inferior end, a cylindrical interior volume 194 for capturing a drilled graft core, and a central aperture 200 that facilitates removal of the graft core.

Figure 8B:
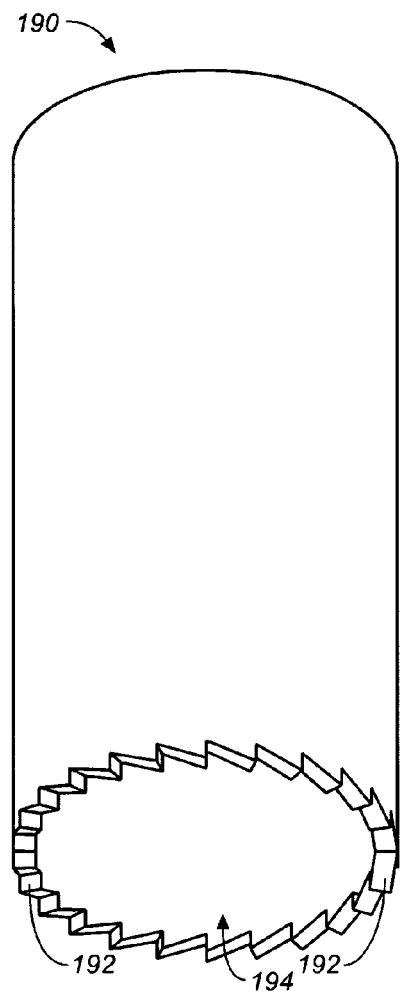
FIG. 8B is a lower perspective view thereof.
Figure 9A:
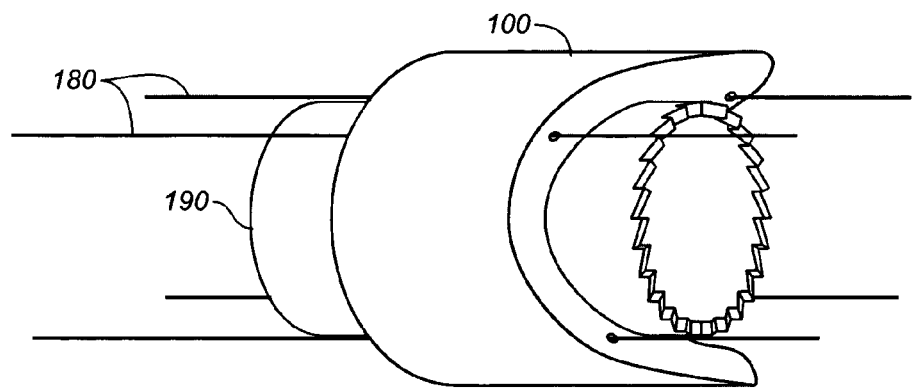
Figure 9B:
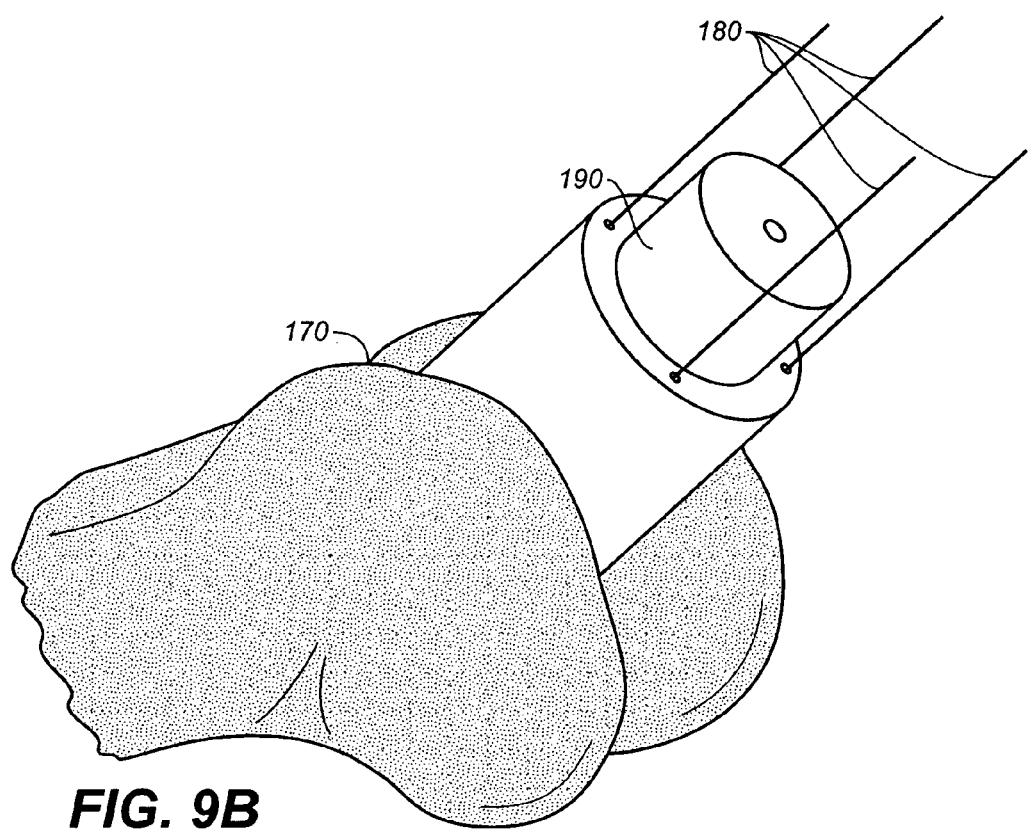
FIG. 9B shows the coring reamer placed on allograft femur.

FIG. 9A is a schematic perspective view showing the outer contoured guide 70 with its circumferential peripheral apertures 80 having small guidewires 180 inserted therethrough, and its central aperture 74 surrounding the cylindrical coring reamer 190 shown in FIG. 8. In FIG. 9B there is shown in perspective view a schematic representation of the combination from FIG. 9A placed onto the allograft femoral trochlea 170.

Figure 10A:
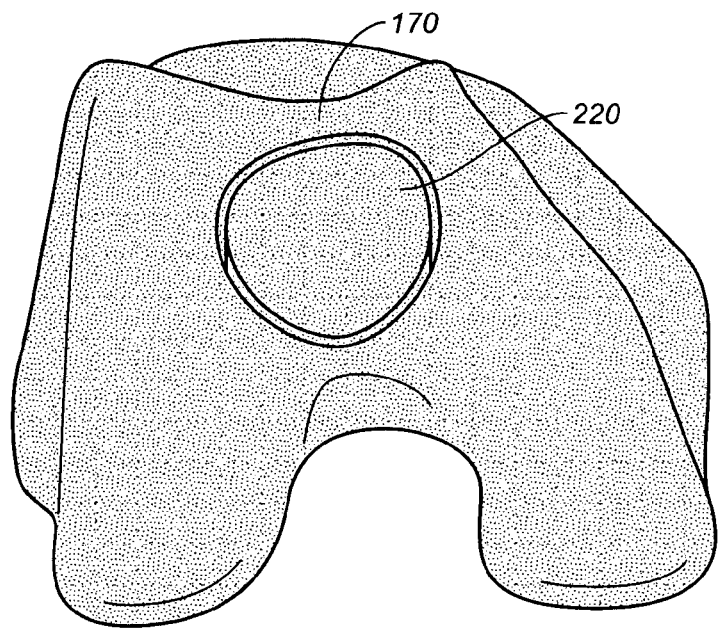
Figure 10B:
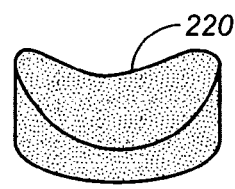
FIGS. 10B and 10C are superior and inferior views, respectively, showing the allograft cores taken from the allograft femoral trochlea using the coring reamer of FIGS. 8A through 9B.
Figure 10C:
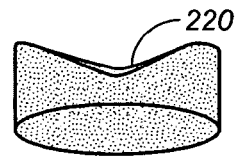

FIG. 10A shows the allograft femoral trochlea 170 after removal of the combination contoured outer guide and reamer of FIG. 9A. Using a variety of techniques, well known to those skilled in the art of orthopaedic surgery, the allograft core 220 can be removed from the allograft femur with variable thicknesses of attached bone. FIGS. 10B and 10C demonstrate the superior and inferior views of the allograft core after removal from the allograft femur. The thickness of attached bone can vary from 5 mm to 50 mm, depending on the surgeon's preference and the specific location.

Figure 6A:
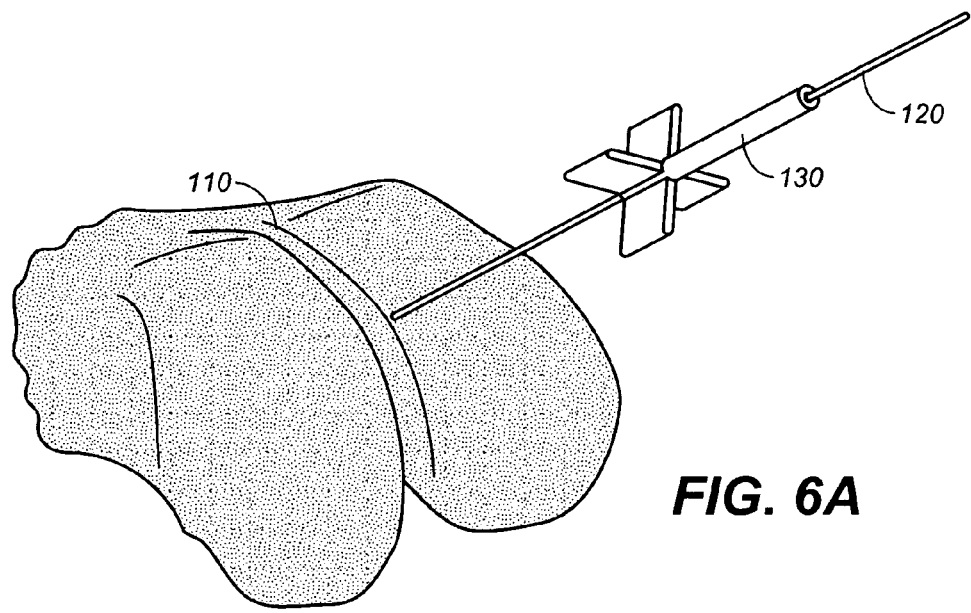
Figure 6B:
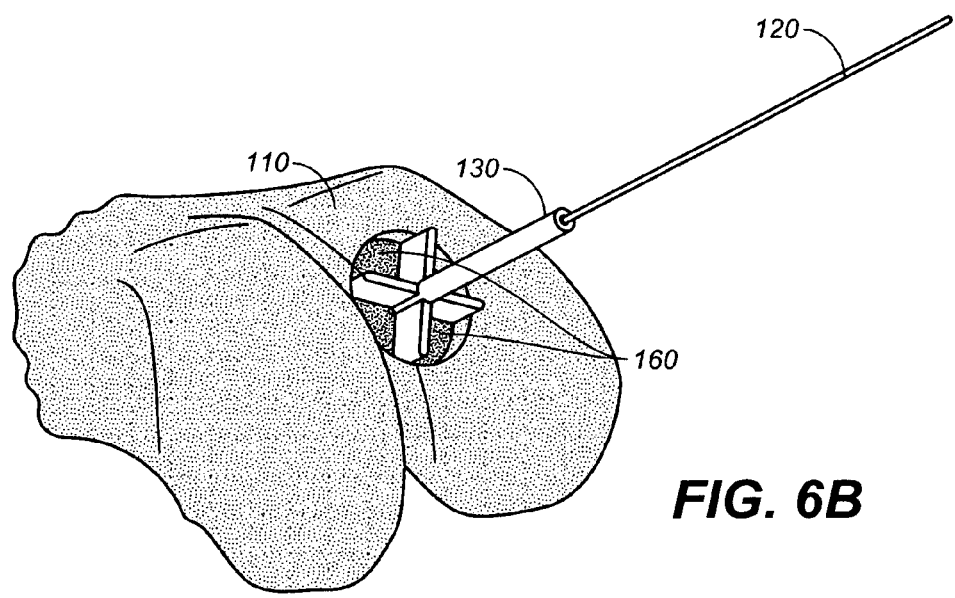
FIG. 6B shows the reamer in operation at the designated site.
Figure 11A:
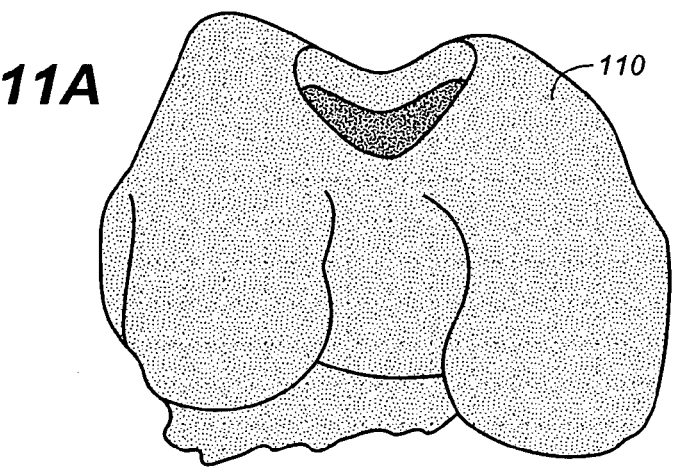
Figure 11B:
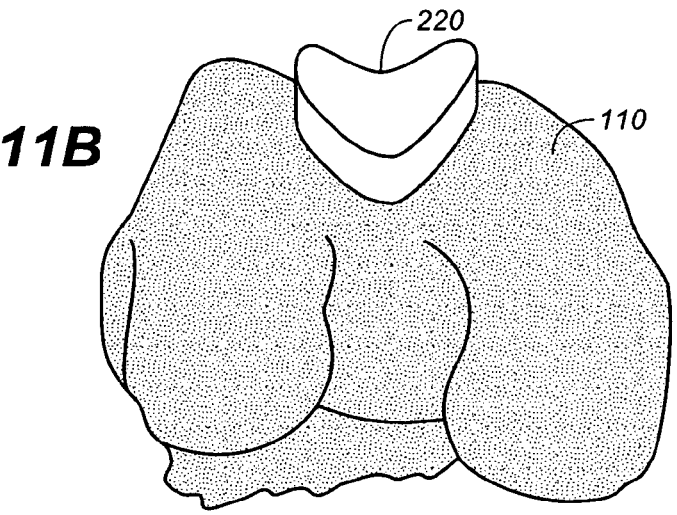
FIGS. 11B-11C show the allograft core implantation into the recipient site.
Figure 11C:
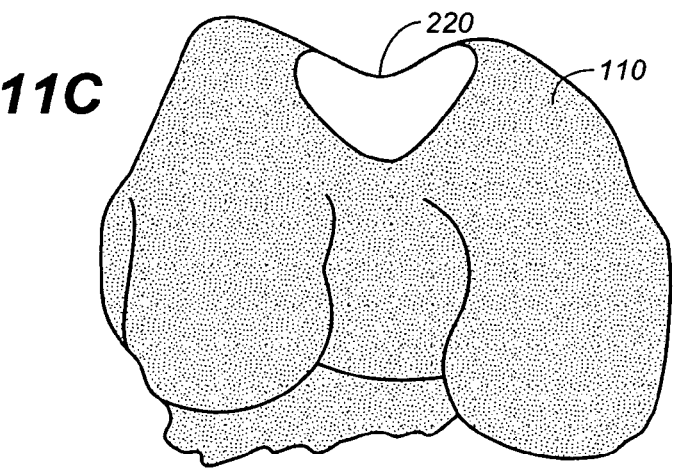

FIG. 11A is a schematic perspective representation of the recipient femoral trochlea 110 from FIG. 6B after removal of the central guidepin. The allograft core 220 is placed into the recipient site and is partially seated in FIG. 11B and fully seated in FIG. 11C.

Figure 12A:
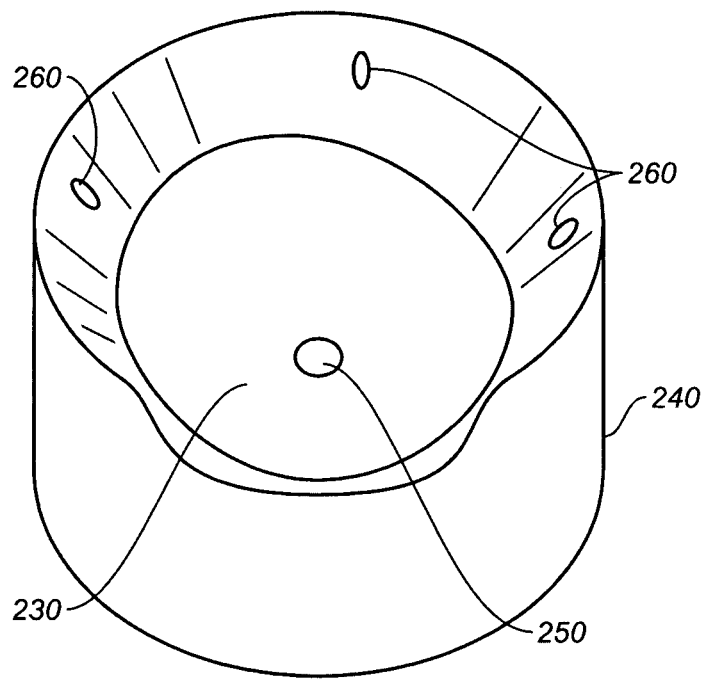
FIGS. 12A and 12B are, respectively, perspective views of the inner and outer contoured posterior femoral guides of a second preferred embodiment of the present invention, these being adapted for use in reconstructing a posterior femoral condyle of the human knee.
Figure 12B:
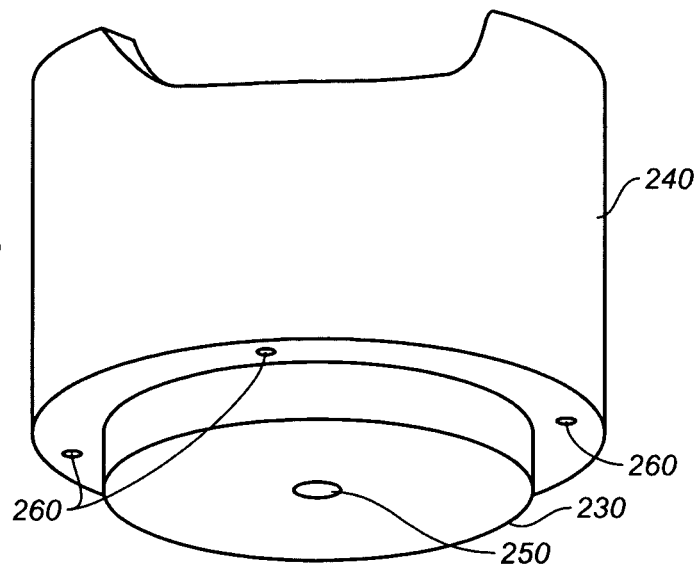

FIGS. 12A and 12B show an alternative embodiment of inventive device adapted for use in preparing and implanting osteochondral allografts for the posterior femoral condyle of the human knee. The inner contoured guide 230 and the outer contoured guide 240 can be made in a variety of surface contours and sizes. In FIGS. 12A and B, the superior and inferior views, respectively, of the posterior femoral condylar guides are shown. The inner guide contains a central aperture 250 for placement of a guidepin into the recipient posterior femoral condyle, analogous to the femoral trochlear guides shown in FIG. 4. The outer guide contains peripheral circumferentially located apertures 260 for fixation to the allograft posterior femoral condyle.

Figure 13A:
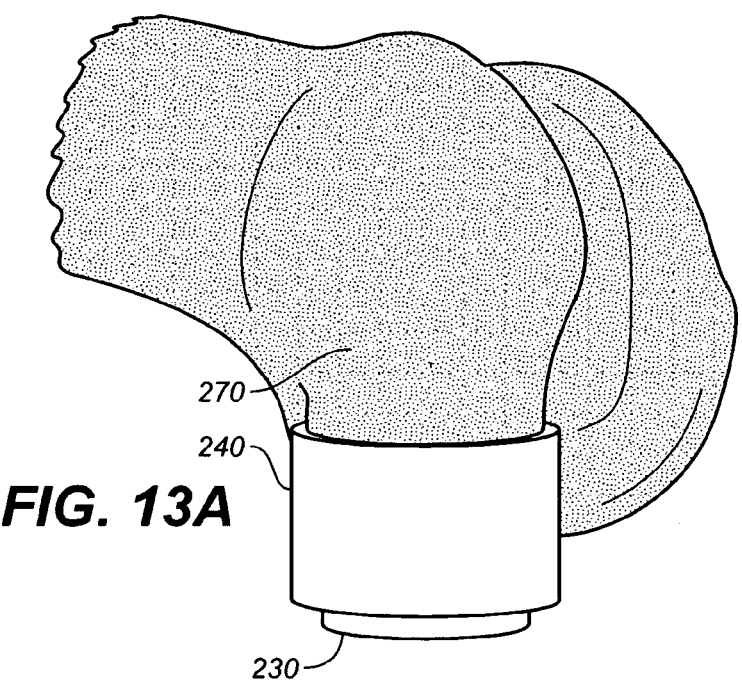
FIGS. 13A and 13B each show the posterior femoral guides placed on the femoral condyle.
Figure 13B:
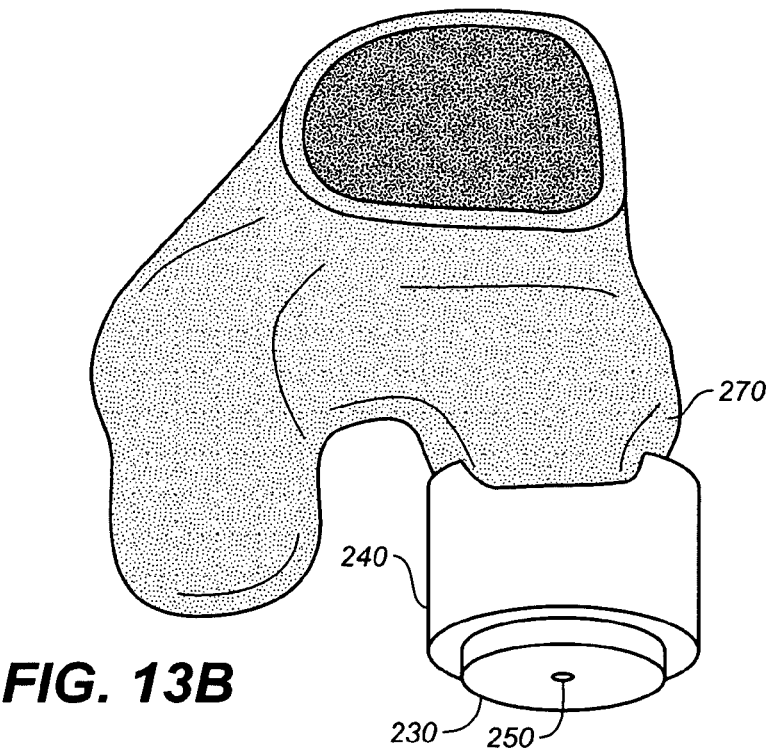

FIGS. 13A and B are perspective views showing the posterior femoral inner and outer contoured guides placed on the femoral condyle 270 prior to placement of the central guidepin in the inner guide aperture 250. Once this has been achieved, the core is harvested in the same fashion as shown for the trochlea in FIGS. 7-10.

Figure 14A:
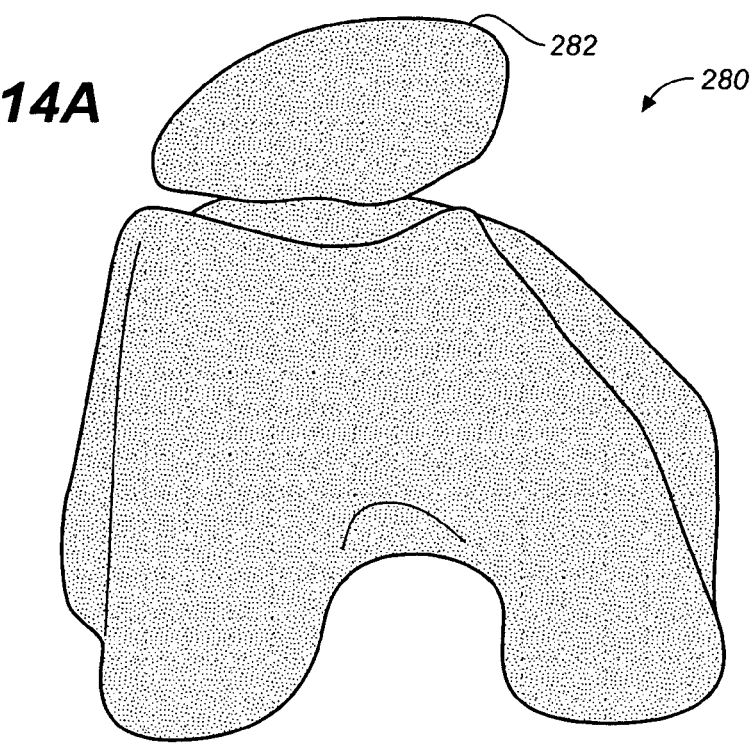
Figure 14B:
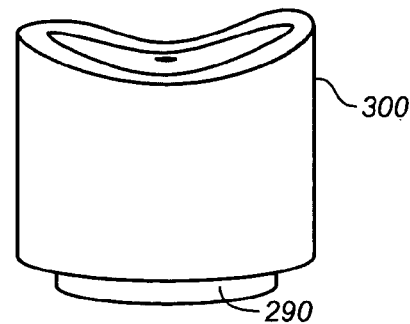
FIGS. 14B and 14C are, respectively, a perspective view showing the contoured guides and the contoured guide fit to the patella.
Figure 14C:
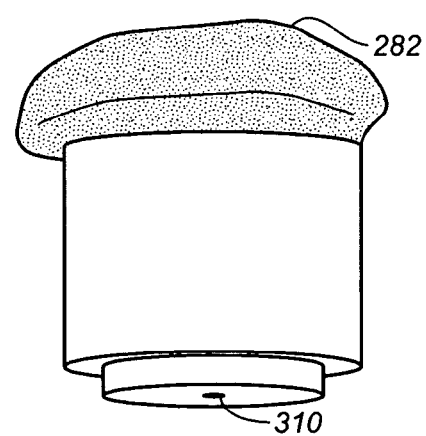

FIG. 14A is a perspective view showing a reconstruction of the human knee 280, including the patella 282. FIG. 14B is a representation of the embodiment of the present invention aimed at treating the patella with an inner contoured guide 290 and an outer contoured guide 300 matched to the articular surface of the patella. After exposure of the articular surface of the patella, the guides are placed on the articular surface of the patella such that the central aperture 310 of the inner guide can be used for passage of a central guidepin. The recipient site reamer shown in FIGS. 6A and 6B can be used to prepare a recipient site on the patella to the desired depth. Next, an allograft patellar core can be implanted in the identical fashion as has been described for the femoral trochlea shown in FIGS. 7-10.

Figure 15A:
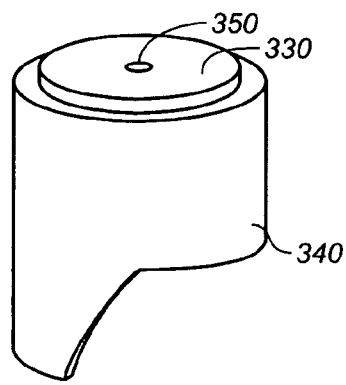
FIGS. 15A through 15C are perspective views shows an alternative embodiment of contoured inner and outer guides adapted for use in reconstructing a human talus.
Figure 15B:
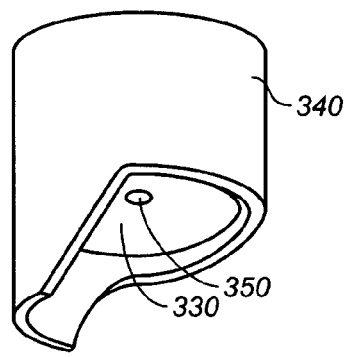
Figure 15C:
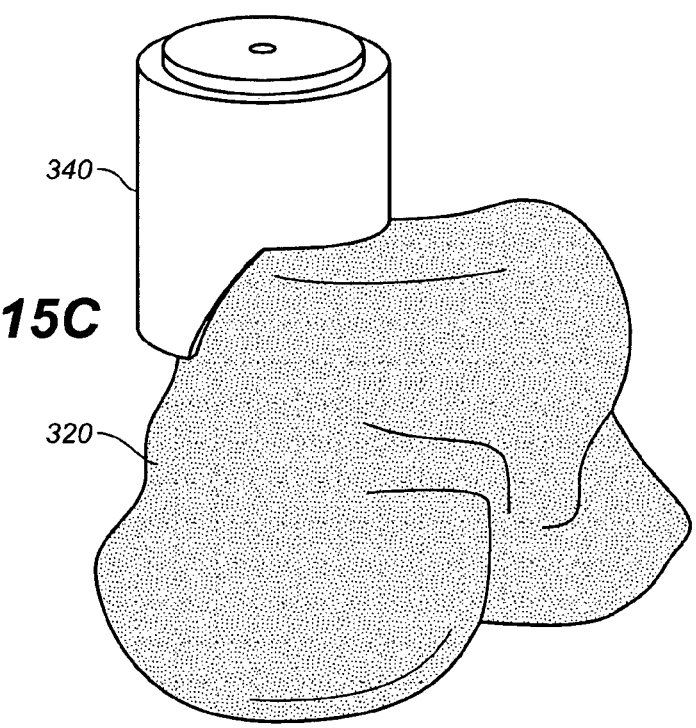

FIG. 15 shows yet another embodiment of the present invention, this one adapted for use in treating the human talus 320. Specific guides contoured to the central, medial, and lateral aspects of the talar dome in various sizes can be manufactured. In FIGS. 15A and B, the superior and inferior views respectively of the contoured inner contoured guide 330 and outer contoured guide 340 are demonstrated. After placement and full articular contact of both guides on the surface, a central guidepin is placed in the central aperture 350 of the inner guide and into the recipient defect. In FIG. 15C, there is shown a perspective view of the medial talus 320 with both guides placed on the articular surface. The subsequent technique for preparation of the allograft core for the talus follows the technique shown previously for the femoral trochlea in the preceding figures.

Figure 16A:
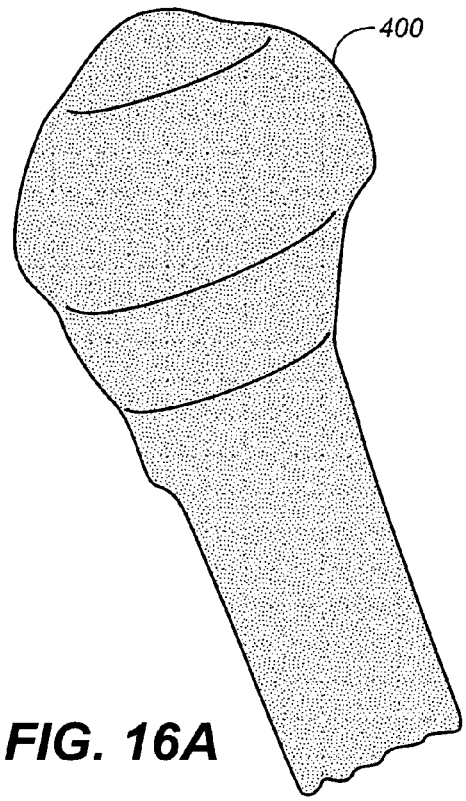
FIGS. 16A through 16C are perspective views shows an alternative embodiment of contoured inner and outer guides adapted for use in reconstructing a humeral head.
Figure 16B:
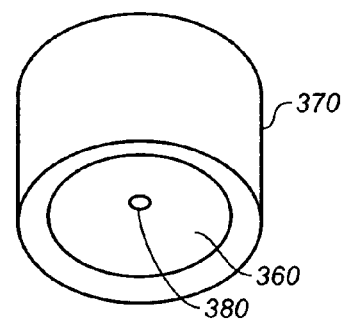
Figure 16C:
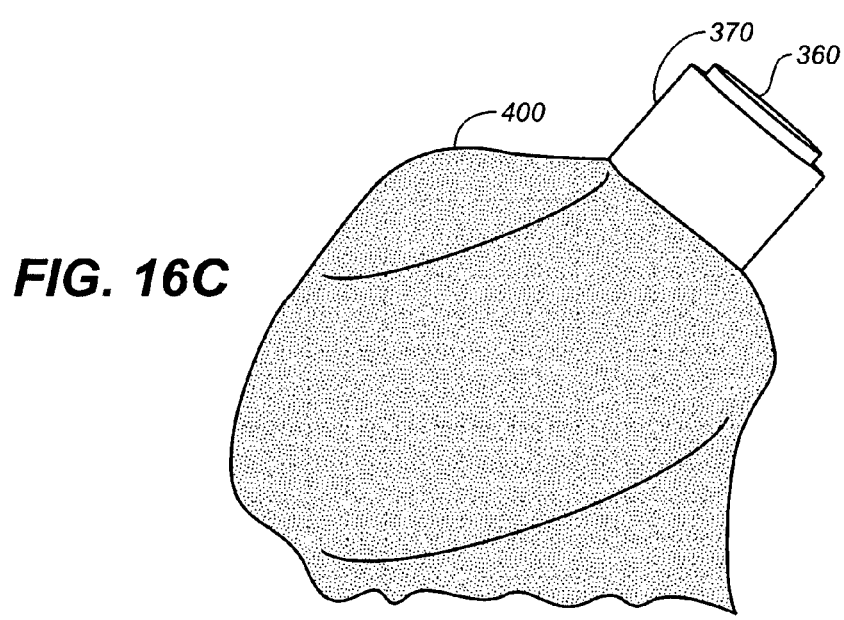

FIGS. 16A-16C show another embodiment of the present invention, this being adapted for use in treating the human proximal humerus. FIG. 16A is a perspective view of a human proximal humerus 400. In FIG. 16B, an inferior view of the combination of inner contoured guide 360 and outer contoured guide 370 matching the radius of curvature and contour of the humeral articular surface is shown. In FIG. 16C, the inner and outer guide combination is placed on the articular surface of the humerus 400 immediately prior to placement of a central guidepin in the aperture 380 (see FIG. 16B) of the inner guide. The remaining portion of the preparation of both the recipient and the donor grafts is identical to that shown for the femoral trochlea in the preceding figures.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

The invention claimed is:

1. An apparatus for the preparation and implantation of osteochondral allografts in human joints, said apparatus comprising:
a cylindrical outer guide having a superior end and a contoured inferior end and a plurality of spaced apart axially disposed circumferential through holes extending from the superior end to the inferior end through said cylindrical outer guide for the insertion of guide wires therethrough for stabilizing said apparatus on donor bone for allograft core harvesting and on a recipient bone site for site preparation, said cylindrical outer guide having an axially oriented cylindrical central through aperture extending from the superior end to the inferior end through said cylindrical outer guide, wherein said contoured inferior end of said cylindrical outer guide includes at least two opposing curvatures configured to mate flush with the condyles of a joint having more than one condyle, said opposing curvatures are separated from one another by at least two opposing projections configured to fit into an intercondylar notch of the joint, and
a cylindrical inner guide removably disposed in the cylindrical central through aperture of said cylindrical outer guide, said cylindrical inner guide having a superior end, a contoured inferior end, and a body portion having a cylindrical outer surface, and including an axially disposed central through aperture extending through said cylindrical inner guide from said superior end to said contoured inferior end of said cylindrical inner guide, the central through aperture is provided through said cylindrical inner guide for the placement of a central guide pin therethrough to stabilize both said cylindrical outer guide and said cylindrical inner guide upon surface contact with the articular surface of the joint and to identify the geometric center of both the donor osteochondral allograft core and the recipient site;
wherein the contour of said inferior end of said cylindrical inner guide and the contour of said inferior end of said cylindrical outer guide are matched with joint-specific articular contours based on the specific anatomical location of the planned surgical procedure such that both of said inferior end of said cylindrical inner guide and said inferior end of said cylindrical outer guide are contoured to achieve full surface contact with both the donor bone site and the recipient bone site; and
wherein said cylindrical outer guide includes a substantially planar superior rim and said cylindrical inner guide includes an expanded rim disposed around said body portion proximate said superior end of said cylindrical inner guide and which is seated on said superior rim when inserted into said cylindrical central through aperture of said cylindrical outer guide.

2. The apparatus of claim 1, further including a guidepin inserted into the central aperture of said inner guide to stabilize both of said inner and outer guides to donor bone or recipient bone.

3. The apparatus of claim 1, further including a recipient site reamer having a plurality of cutting blades.

4. The apparatus of claim 3, wherein said recipient site reamer comprises a tubular body portion with an axially disposed through hole and a plurality of cutting blades radially extending from said body portion.

5. The apparatus of claim 4, further including a cylindrical coring reamer for harvesting an allograft core, said coring reamer having a radius larger than the radius of said recipient site reamer, the latter radius as measured from the center of said axially disposed through hole and the edge of any one of said plurality of cutting blades.

6. The apparatus of claim 4, further including a cylindrical coring reamer for harvesting an allograft core, said coring reamer having a radius larger than the radius of said recipient site reamer, the latter radius as measured from the center of said axially disposed through hole of the tubular body portion of the recipient site reamer and the edge of any one of said plurality of cutting blades of the recipient site reamer.

7. The apparatus of claim 1, wherein said inner guide and said outer guide are matching guides adapted for use in the preparation and implantation of osteochondral allografts in a human knee, hip, or shoulder.

* * * * *